United States Patent [19]

Smith, Jr.

[11] 4,215,011

[45] Jul. 29, 1980

[54] CATALYST SYSTEM FOR SEPARATING ISOBUTENE FROM C₄ STREAMS

[75] Inventor: Lawrence A. Smith, Jr., Houston, Tex.

[73] Assignee: Chemical Research and Licensing Company, Houston, Tex.

[21] Appl. No.: 13,730

[22] Filed: Feb. 21, 1979

Related U.S. Application Data

[63] Continuation-in-part of Ser. No. 928,397, Jul. 27, 1978.

[51] Int. Cl.² .................... B01J 31/08; B01J 35/02
[52] U.S. Cl. ........................ 252/426; 252/477 R; 203/DIG. 6
[58] Field of Search ............ 252/477 R, 426; 203/DIG. 6

[56] References Cited

U.S. PATENT DOCUMENTS

| 2,403,672 | 7/1946 | Matuszak | 203/DIG. 6 |
| 3,317,593 | 5/1967 | Enk et al. | 260/540 |
| 3,531,539 | 9/1970 | Tidwell | 260/677 |
| 3,629,478 | 12/1971 | Haunschild | 260/677 A |
| 3,634,534 | 7/1972 | Haunschild | 260/677 A |
| 4,027,476 | 6/1977 | Schmidt | 252/477 R |

*Primary Examiner*—W. J. Shine
*Attorney, Agent, or Firm*—Kenneth H. Johnson

[57] ABSTRACT

A component of a distillation system having both a catalytic function and a distillation function.

7 Claims, 3 Drawing Figures

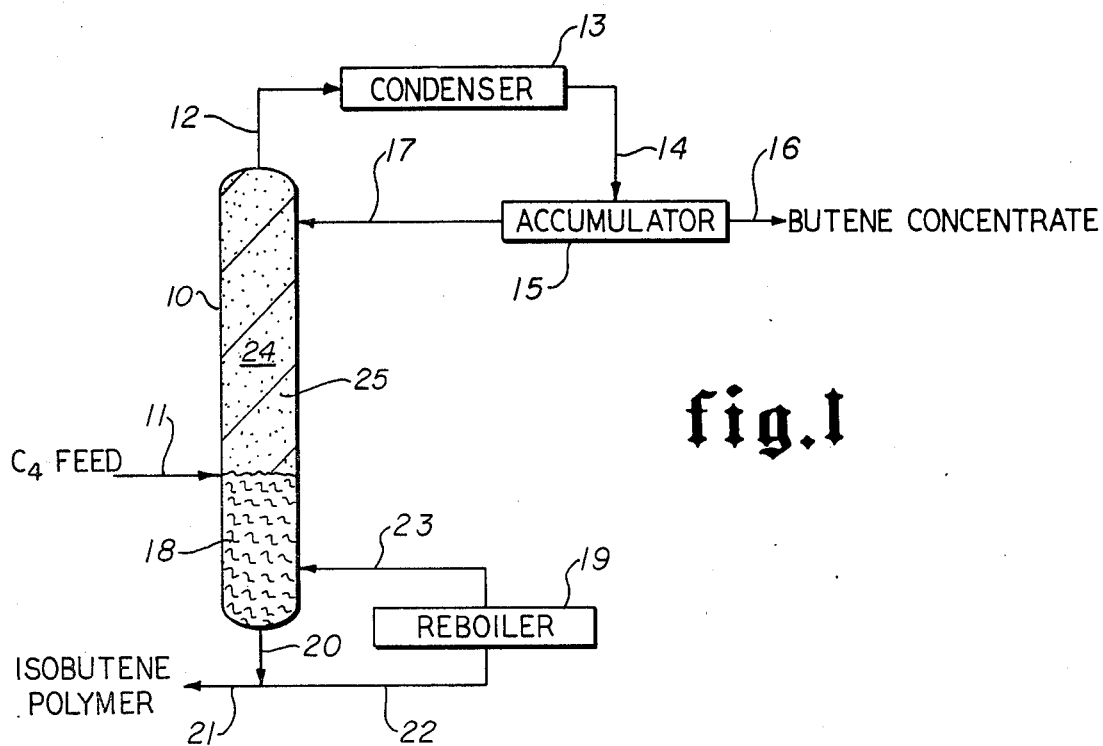
fig.1
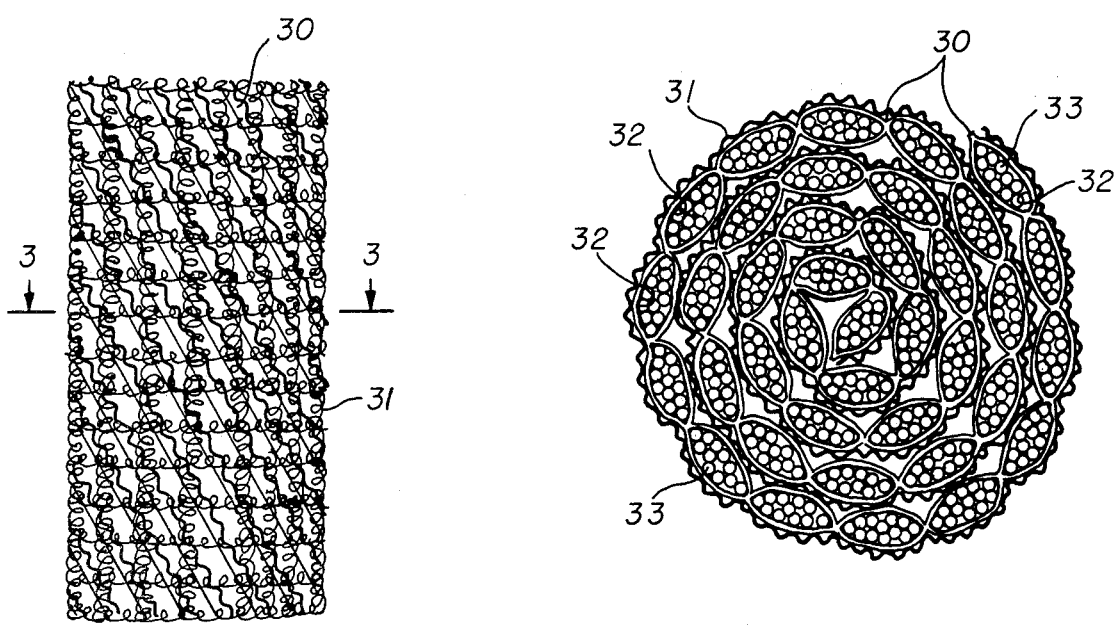
fig.2
fig.3

CATALYST SYSTEM FOR SEPARATING ISOBUTENE FROM C$_4$ STREAMS

This application is a continuation-in-part of Ser. No. 928,397, filed July 27, 1978, filed as the result of a restriction requirement.

BACKGROUND OF THE INVENTION

1. Field of the Invention

The present invention relates to the separation of isoolefins from streams containing mixtures of an isoolefin and the corresponding normal olefin. The present invention is especially useful for the separation of isobutene from streams containing n-butenes.

2. Description of the Prior Art

Isoolefins of 4 carbon atoms are difficult to separate from the corresponding normal olefin by simple fractionation because of the closeness of their boiling points. In prior art processes are generally practiced commercially, the isoolefin is selectively absorbed by sulfuric acid and the resulting isoolefin-containing sulfuric acid extract is then diluted and heated or treated with steam to separate the isoolefin.

Isobutene and diisobutene are of significant value having diverse applications, for example, isobutene is one of the comonomers for butyl rubber and diisobutene is an intermediate in the preparation of detergents. The n-butenes are required in pure form for homopolymerization and as feeds for the oxidative production of butadiene. One manner of separating these components is to pass the mixture through what is called a cold acid extraction procedure wherein the stream is fed into a bath of concentrated sulfuric acid. Separation is achieved by virtue of the solubility of the isobutene in the sulfuric acid, the n-butenes and other hydrocarbons present passing overhead.

In an improved process reported in U.S. Pat. No. 3,531,539 to Tidwell, the C$_4$ feed stream containing isobutene was contacted with a molecular sieve at an elevated temperature and under sufficient pressure to maintain a liquid phase, wherein the isobutene is converted to diisobutene which is easily separated from the stream by conventional separation techniques.

SUMMARY OF THE INVENTION

The present invention is a method for the separation of isoolefins, preferably having four to six carbon atoms, from streams containing mixtures thereof with the corresponding normal olefins. For example, streams containing isobutene and normal butene, isopentene and normal pentene and isohexene and normal hexene.

The method of the invention comprises (a) feeding a mixture containing an isoolefin and the corresponding normal olefin to a distillation column reactor into a feed zone, (b) concurrently: (1) contacting said mixture with a fixed bed acidic cation exchange resin, hereby catalytically reacting the isoolefin with itself to form a dimer, and (2) fractionating the resulting mixture of dimer and normal olefin, (c) withdrawing the dimer from the distillation column at a point below said feed zone and (d) withdrawing the normal olefin from the distillation column reactor at a point above the feed zone, preferably above the acidic cation exchange resin.

A particular embodiment of the present invention is a method for the separation of isobutene from a mixture comprising n-butene and isobutene. More generally, the invention is suitable for the separation of isobutene from a hydrocarbon stream which is substantially C$_4$ hydrocarbons, such as n-butane, isobutene, n-butene, isobutane, and butadiene (minor amounts of C$_3$ and C$_5$ hydrocarbons, i.e., less than 10% may be incidental components of such C$_4$ stream).

Briefly stated, the present method for separating isobutene comprises:

(a) feeding a mixture containing isobutene and n-butene to a distillation column reactor into a feed zone, (b) concurrently:
(1) contacting said mixture with a fixed bed acidic cation exchange resin, thereby catalytically reacting isobutene with itself to form diisobutene, and
(2) fractionating the resulting mixture comprising diisobutene and n-butene, (c) withdrawing said diisobutene from said distillation column reactor at a point below said feed zone and, (d) withdrawing n-butene from said distillation column reactor at a point above the feed zone.

The present invention also provides a new method for the preparation of dimer, such as diisobutene.

The reaction system can be described as heterogeneous since the catalyst remains as a distinct entity. The catalyst may be employed in such conventional distillation packing shapes, as Raschig rings, Pall rings, saddles or the like. Similarly, the resin may be employed in a granular or bead form.

The catalyst-packing material is a central feature of the invention, clearly without it the process as described can not be carried out. The shaped catalyst which is employed may also be employed in other processes, such as liquid phase contact with aqueous or organic systems to carry out procedures known in the art, and which may be carried out with catalyst in the prior art in other forms such as beads, pellets or the like. It should be appreciated that the distillation functional catalyst compositions of the present invention provide a more open packing as is required for distillation, hence if the present catalyst-packing is employed in a liquid phase process, a larger bed will be required to obtain the comparable degree of liquid-catalyst contact as compared for example to close packed solid beds of small beads.

The particular shape of the catalytic material is not critical, so long as the shape functions as a distillation packing. Thus, balls, chunks, sheets, tubes or spirals of catalytic material may be employed as well as the conventional distillation shapes noted above.

Reticulated polymer foams of catalytic material may be employed. However, the foam would not be employed as a solid mass, since the pressure drops through such foams, even though they are largely devoid of cell walls is still too high and unacceptable for use as a distillation packing. The foam can be cut or stamped into usable shapes or sheets wound in a spiral in the distallation column to allow vapor passage through the column. The spiral reticulated sheets will function in a similar manner to the cloth bags of resin beads described herein.

The catalytic material may be any material appropriate for the reaction at hand, that is, it may be an acid catalyst (for the reaction described herein an acid catalyst is required) or a basic catalyst or others such as catalytic metals and their oxides or halides suitable for a multitude of catalytic reactions and of course is heterogeneous with the reactants or other fluids in the system.

For example, a different reaction is the preparation of formic acid from methanol using iron oxide or transesterification using a base catalyst such as NaOAl.

The term "catalyst" or "catalytic material" is used to include any solid material which is recognized for the reaction under consideration as performing as a catalyst therein.

Thus, the catalytic material is more than that in the present invention. It is a distillation part or component since it is also the distillation packing (note there may be inert distillation packing in the column also, such as, below or above the catalytic packing, between beds of catalytic packing or intermixed into the catalytic packing). Thus, broadly stated, the catalytic material is a component of a distillation system functioning as both a catalyst and a distillation packing, i.e., a packing for a distillation column having both a distillation function and catalytic function.

It has been found that the resin beads in a conventional fixed bed form too compact a mass for the upward flowing vapor and downward flowing liquid. However, it has been found that by placing the resin beads into a plurality of pockets in a cloth belt, which is supported in the distillation column reactor by open mesh knitted stainless steel wire by twisting the two together, allows the requisite flows, prevents loss of catalyst, allows for the normal swelling of the beads and prevents the breakage of the beads through mechanical attrition. This novel catalyst arrangement is also part of the present invention.

Thus, the present invention includes a catalyst system for use in reaction-distillation columns comprising a plurality of closed cloth pockets containing a particulate catalytic material, arranged and supported in said reaction-distillation by wire mesh intimately associated with said closed cloth pockets. In particular, there are a plurality of said pockets in a single cloth belt, said cloth being coiled into a spiral and having wire mesh disposed between the coils of said cloth belt spiral. Preferably the pockets are substantially parallel to the axis of the spiral and the pockets elongated along this axis. Normally in the catalyst system a plurality of coiled cloth belts as described are arranged vertically in a column.

The cloth may be of any material which is not attacked by the hydrocarbon feed or products under the conditions of the reaction. Cotton or linen may be used, however, fiber glass is preferred. Briefly, a preferred catalyst system comprises a plurality of closed cloth pockets containing particulate catalytic material arranged and supported in said distillation column reactor by wire mesh intimately associated therewith.

The particulate catalytic material may be a powder, small irregular fragments or chunks, small beads and the like. The particular form of the catalytic material in the cloth pockets is not critical, so long as sufficient surface area is provided to allow a reasonable reaction rate. This sizing of catalyst particles can be best determined for each catalytic material (since the porosity or available internal surface area will vary for different materials and of course affects the activity of the catalytic material).

What readily distinguishes the present method from the prior art is that the prior art has consistently employed a continuous liquid phase system for contacting the isoolefin with the acidic catalyst, whereas the present invention is carried out the method in a catalyst packed distillation column which can be appreciated to contain a vapor phase and some liquid phase as in any distillation. The dimerization reaction of isobutene and the fractionation of the resultant n-butene-dimer mixture is carried out simultaneously, i.e., concurrently. That is as the dimer is formed in the catalyst bed, the lower boiling n-butene is fractionated away in the catalyst bed and removed overhead while the high boiling dimer drops to the lower portion of the column.

The bulk-type liquid phase reactions of the prior art had as one problem the control of the temperature. The distillation avoids this problem entirely.

DRAWINGS

FIG. 1 is a schematic representation of a catalytic distillation column for use in this invention.

FIG. 2 is an elevational view of a catalyst belt packing.

FIG. 3 is a cross sectional view of the catalyst belt packing taken along 3—3 of FIG. 2.

DETAILED DESCRIPTION OF THE INVENTION AND SPECIFIC EMBODIMENTS

Mixed $C_4$ streams containing principally isobutane (I-$C_4$), normal butane (n-$C_4$), butene-1 (B-1), isobutene (I-B), trans butene-2 (TB-2) and cis butene-2 (CB-2) (plus some minor impurities including butadiene), can be treated with cold sulfuric acid to remove isobutene and produce a butylene concentrate. The isobutene removed is recovered from the acid as a polymer (mostly dimer). The isobutene dimer (i.e., some other isobutene polymers as well) and butene concentrate are valuable products.

A substitute route for accomplishing this same separation has been discovered. It has been found that a distillation column packed with a properly supported acid catalyst can produce a bottom stream containing isobutene polymer (mostly dimer) and an overhead stream that is relatively free of isobutene. This is surprising since the catalyst used would normally produce mostly heavy isobutene polymers and copolymers if the reaction were conducted in a conventional fixed bed.

The success of the catalytic distillation approach lies in an understanding of the principles associated with distillation. First, because the reaction is occurring concurrently with distillation, the initial reaction product, diisobutene, is removed from the reaction zone nearly as quickly as it is formed. This removal of isobutene dimer minimizes further chaining to larger polymer lengths. Second, because all the $C_4$ components are boiling, the temperature of the reaction is controlled by the boiling point of the $C_4$ mixture at the system pressure. The heat of reaction simply creates more boil up, but no increase in temperature. Third, the reaction has an increased driving force because the reaction products have been removed and can not contribute to a reverse reaction (LeChatelier's Principle).

As a result, a great deal of control over the rate of reaction and distribution of products can be achieved by regulating the system pressure. Also, adjusting the throughput (residence time = liquid hourly space velocity$^{-1}$) gives further control of product distribution and degree of isobutene removal.

The temperature in the reactor is determined by the boiling point of the $C_4$ at any given pressure, that is, at constant pressure a change in the temperature of the system, indicates a change in the composition in the column. Thus, to change the temperature the pressure is changed. By increasing the pressure, the temperature in the system is increased. Generally, pressures in the range of 0 to 400 psig are or may be employed, preferably 30 to 150 psig. For the C$_4$ stream, the present reaction will be carried out generally at pressures in the range of 10 to 300 psig, which will generally mean temperatures in the range of 10° to 100° C.

The reaction of isobutene with itself is equilibrium limited; however, by carrying out the reaction in a distillation column reactor and fractionating the formed product (diisobutene) downward away from the reaction zone, the equilibrium is constantly disrupted and hence the reaction never comes to equilibrium. This has the advantage of course, of achieving an effective 100% conversion (provided the catalyst bed is of sufficient length such that none of the isobutene escapes therefrom to go overhead with the n-butenes). The adjustment of the size of the catalyst bed is a mere mechanical step to be determined for each reactor and in accordance with the reaction conditions.

The system would normally be considered anhydrous; however, small amounts of water often saturate the feed stream and represent about 400 to 600 ppm thereof. The process will continue to operate in the same fashion, in the presence of this amount of water; however, the following effects have been observed: (1) all of the rates increase, however, the lower rates increase faster. (Although not mentioned above, those in the art will recognize that there is a reaction of isobutene with butene to produce "codimeter". This rate is normally much slower than the diisobutene rate). (2) the amount of codimer increases and (3) teritary butanol is produced in small amounts.

The feed to the distillation column reactor is made at the lower end of the catalyst bed, preferably into the catalyst to allow immediate contact of the isobutene with the catalyst.

A reflux is preferably included in the system. The reflux ratio could vary over the range of 1 to 20:1. In practice, the higher ratio may be used to compensate for a short catalyst bed such as required for experimental work. In commercial size unit the catalyst bed would be provided so that lower reflux and hence higher unit productivity could be obtained.

The cation resins are those which have been used in the prior art for this reaction. Catalysts suitable for the new process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzenes, divinyl toluenes, divinylphenylethers and others. The polymers may be prepared in the presence of absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C., and the sulfuric acid should contain sufficient sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,247).

The ion exchange resin is preferably used in a granular size of about 0.25 to 1 mm, although particles from 0.15 mm up to about 1 mm may be employed. The finer catalysts provided high surface area, but also result in high pressure drops through the reactor. The macroreticular form of these catalysts is preferred because of the much larger surface area exposed and the limited swelling which all of these resins undergo in a non-aqueous hydrocarbon medium.

Similarly, other acid resins are suitable, such as perflurosulfonic acid resins which are copolymers of sulfonyl fluorovinyl ethyl and fluorocarbon and described in greater detail in DuPont "Innovation", Volume 4, No. 3, Spring 1973 or the modified forms thereof as described in U.S. Pat. Nos. 3,784,399; 2,770,567 and 3,849,243.

FIG. 1 illustrates schematically a typical distillation column in which the present process may be carried out. The column 10 was a one inch diameter, five foot tall tube containing two feet of conventional glass 1/16 inch helices 18 and three feet of the catalytic packing as shown in FIGS. 2 and 3.

FIG. 2 shows a cloth belt 30 wrapped in open mesh knitted stainless steel wire 31. The cloth bag 30 is composed of a plurality of vertical pockets 32 sewn into the bag as shown in FIG. 3. Each pocket 32 is filled with resin catalyst 33. The catalyst system may comprise a plurality of pockets in a single cloth belt, the cloth belt being coiled into a spiral and having the wire mesh disposed between the coils of the cloth belt spiral and the pockets are substantially parallel to the axis of said spiral.

The wire mesh provides the support for the catalyst (belt) and provides some degree of vapor passage through the catalyst beads, which otherwise form a very compact bed which has a high pressure drop. Thus, the down flowing liquid is in intimate contact with the rising vapors in the column.

In commercial-scale operations, it is contemplated, catalyst packing would be made up of alternating layers of resin-filled cloth belts similar to the ones described above, and a spacing material which could be of any convenient, suitable substance, such as a corrugated wire screen or wire cloth or a knitted wire mesh. The layers would be arranged vertically to provide vapor passages between the belts. The cylindrical resin-filled pockets could be oriented either vertically or horizontally. For simplicity of fabrication and for better distribution of vapor flow passages, a vertical orientation is preferred i.e., the pockets are elongated along the axis of said spiral. The height of a section of this packing could be of any convenient dimension, from a few inches to several feet. A catalyst system would preferably comprise a plurality of cloth belts as described arranged in a column, preferably arranged vertically in said column. For ease of assembly and installation, the packing would be made into sections of the desired shape and size, each section fastened together with circumferential bands or tie wires depending on its size and shape. A complete assembly in a column would consist of several sections, arranged in layers, with the orientation of the resin-filled belts turned at right angles in successive layers to improve liquid and vapor flow distribution.

Other configurations which may be useful but with certain draw backs would be cages of wire cloth to contain catalyst beads, immersed in liquid on a conventional sieve tray. Disadvantages would be the restriction of vapor flow by the close weave of the wire, which may be compensated by allowing the beads to move freely in the cage, thereby causing attrition. Similarly, suspension of the catalyst on a tray would present problems of attrition, maintaining suspension and preventing catalyst from leaving the tray.

In the laboratory column the bags are made in the form of a cloth belt approximately six inches wide with narrow pockets approximately ¾ inch wide sewn across the belt. The pockets are spaced about ⅛ inch apart. These pockets are filled with the catalyst beads to form approximately cylindrical containers, and the open ends are then sewn closed to confine the beads. This belt is then twisted into a helical form to fit inside the one inch column. Twisted in with the belt is also a strip of an open mesh knitted stainless steel wire, which serves to separate the resin filled cloth pockets and provide a passage for vapor flow.

In operation, the isobutene containing C$_4$ feed enters through line 11 into the lower end of the catalytic zone 24 which contains the catalyst bag belt 25 as described. The temperature and pressure in the column are such that the C$_4$ boils up in the column, however, as the isobutene contacts the catalyst, dimer is formed, which being higher boiling than the C$_4$ stream, passes to the bottom of the reactor where it is removed via line 20 with a portion being recovered through line 21 and another portion recycled into reboiler 19 through line 22 and hence back into the bottom of the column 10 through line 23.

Meanwhile, the n-butenes pass upward through the catalyst zone 24 and out of the column 10 via line 12 to condenser 13 hence into accumulator 15 via line 14. A portion is recovered as butene concentrate from line 16 and a portion is returned as reflux through line 17 into column 10.

EXAMPLES

In the following examples, the feed rate of C$_4$'s to the column is adjusted to maintain a bottoms temperature which would correspond to low C$_4$ concentration. The catalyst employed was Amberlyst 15, manufactured by Rohm and Haas, Philadelphia, Pa. The feed had the following composition:

| Component | mole % |
|---|---|
| isobutane | 2.8 |
| n-butane | 8.6 |
| butene-1 | 24.6 |
| isobutene | 50.5 |
| trans-butene-2 | 10.4 |
| cis-butene-2 | 3.1 |
| butadiene | .5 |

-continued

| Component | mole % |
|---|---|
| ratio butene-1/butene-2 | 1.8 |

EXAMPLE 1

System Pressure = 70 psig
Catalytic zone temperature = 60° C.
Results:

| | Mole % component at LHSV$^{-1}$ (Hrs)* | |
|---|---|---|
| Component | 0.2 | 0.7 |
| OVERHEAD: | | |
| isobutane | 5.8 | 4.6 |
| n-butane | 20.0 | 28.7 |
| butene-1 | 31.6 | 15.6 |
| isobutene | 7.4 | 1.5 |
| trans-butene-2 | 26.7 | 37.7 |
| cis-butene-2 | 8.4 | 11.9 |
| butadiene | .18 | .03 |
| ratio butene-1/butene-2 | 1.2 | .3 |
| Overhead take-off (ml/hr) | 480 | 160 |
| bottom temp °C. | 133 | 171 |
| bottom C$_4$'s (mole %) | 9.8 | 2.7 |
| BOTTOM:** | | |
| component | | |
| tert-butyl alcohol | .14 | .04 |
| diisobutene | 61.6 | 51.5 |
| codimer | 18.0 | 31.3 |
| triisobutene | 16.8 | 12.9 |
| heavies | 3.5 | 4.2 |

*LHSV$^{-1}$ is calculated by dividing the overhead take-off rate into the volume of resin in the catalytic zone. (The zone contained 115 grams (190 ml) of catalyst).
**C$_4$'s are normalized out

EXAMPLE 2

System Pressure = 40 psig
Catalytic zone temperature = 40° C.
Results:

| | mole % component at LHSV$^{-1}$ (Hrs)* | |
|---|---|---|
| Component | 0.7 | 1.4 |
| OVERHEAD: | | |
| isobutane | 4.8 | 5.7 |
| n-butane | 15.1 | 16.0 |
| butene-1 | 44.3 | 43.8 |
| isobutene | 12.1 | 9.3 |
| trans-butene-2 | 18.6 | 20.0 |
| cis-butene-2 | 4.8 | 5.1 |
| butadiene | .21 | .2 |
| ratio butene-1/butene-2 | 1.9 | 1.7 |
| Overhead take-off (ml/hr) | 160 | 80 |
| bottom temp °C. | 142 | 159 |
| bottom C$_4$'s (mole %) | 3.0 | .4 |
| BOTTOM:** | | |
| Component | | |
| tert-butyl alcohol | .26 | .11 |
| diisobutene | 75.0 | 74.5 |
| codimer | 10.2 | 12.6 |
| triisobutene | 11.6 | 10.2 |
| heavies | 2.9 | 2.6 |

*LHSV$^{-1}$ is calculated by dividing the overhead take-off rate into the volume of resin in the catalytic zone. (The zone contained 115 grams (190 ml)) of catalyst).
**C$_4$'s are normalized out.

The invention claimed is:

1. A catalyst system for use in a reaction-distillation column comprising a plurality of closed cloth pockets containing a particulate catalytic material, arranged and supported in said reaction-distillation column by wire mesh intimately associated with said closed cloth pockets.

2. The catalyst system according to claim 1 comprising a plurality of said pockets in a single cloth belt, said cloth belt being coiled into a spiral and having wire mesh disposed between the coils of said cloth belt spiral.

3. The catalyst system according to claim 2 wherein said pockets are substantially parallel to the axis of said spiral.

4. The catalyst system according to claim 2 wherein said pockets are elongated along the axis of said spiral.

5. A catalyst system comprising a plurality of coiled cloth belts according to claim 2 arranged in a column.

6. The catalyst system according to claim 5 wherein said coiled cloth belts are arranged vertically in said column.

7. The catalyst system according to claim 1 wherein said particulate catalytic material is acid cation exchange resin.

* * * * *

UNITED STATES PATENT AND TRADEMARK OFFICE
CERTIFICATE OF CORRECTION

PATENT NO. : 4,215,011
DATED : July 29, 1980
INVENTOR(S) : Lawrence A. Smith, Jr.

It is certified that error appears in the above—identified patent and that said Letters Patent is hereby corrected as shown below:

Column 1, line 20 reads "processes are generally" but should read -- processes as generally --

Column 1, line 57 reads "resin, hereby catalyt-" but should read -- resin, thereby catalyt --

Signed and Sealed this

Seventeenth Day of November 1981

[SEAL]

Attest:

GERALD J. MOSSINGHOFF

Attesting Officer

Commissioner of Patents and Trademarks